(12) United States Patent
Lindstrom

(10) Patent No.: US 9,233,123 B1
(45) Date of Patent: Jan. 12, 2016

(54) USE OF OPHTHALMIC COMPOSITIONS INCLUDING LUBRICANT, DETURGESCENT AGENT, AND GLYCOSAMINOGLYCAN

(76) Inventor: Richard L. Lindstrom, Wayzata, MN (US)

( * ) Notice: Subject to any disclaimer, the term of this patent is extended or adjusted under 35 U.S.C. 154(b) by 527 days.

(21) Appl. No.: 12/928,226

(22) Filed: Dec. 7, 2010

(51) Int. Cl.
*A61K 31/737* (2006.01)
*A61K 47/10* (2006.01)
*A61K 47/36* (2006.01)
*A61K 9/00* (2006.01)

(52) U.S. Cl.
CPC .............. *A61K 31/737* (2013.01); *A61K 47/10* (2013.01); *A61K 47/36* (2013.01)

(58) Field of Classification Search
CPC ............ A61K 2300/00; A61K 31/196; A61K 31/573; A61K 9/0048; A61K 31/57; A61K 31/407; A61K 31/722; A61K 31/737; A61K 47/10; A61K 47/36; A61K 45/06; A61K 49/00; A61K 31/13; A61K 31/135; A61K 31/165; A61K 31/44; Y10S 514/912; Y10S 514/915
USPC .......... 424/94.4; 435/1.1; 514/54, 59, 62, 912, 514/915
See application file for complete search history.

(56) References Cited

U.S. PATENT DOCUMENTS

| | | | | |
|---|---|---|---|---|
| 4,486,416 A | * | 12/1984 | Soll et al. | 514/54 |
| 7,820,639 B2 | * | 10/2010 | Lindstrom | 514/54 |
| 2002/0081289 A1 | * | 6/2002 | Neuhann | 424/94.4 |
| 2003/0198630 A1 | * | 10/2003 | Neuhann | 424/94.4 |
| 2006/0073592 A1 | * | 4/2006 | Sun et al. | 435/423 |
| 2009/0017438 A1 | * | 1/2009 | Roy et al. | 435/1.1 |

FOREIGN PATENT DOCUMENTS

WO   WO9520969   *   8/1995

* cited by examiner

*Primary Examiner* — Debbie K Ware
(74) *Attorney, Agent, or Firm* — Lawoffices of Steven W. Weinrieb

(57) ABSTRACT

Ophthalmic compositions including lubricant agent, deturgescent agent, glycosaminoglycan, and water are used to preserve tissue in vitro; for example, ocular tissue, especially a cornea, thereby facilitating subsequent transplant, especially of a complete cornea. Preferably, the ophthalmic composition and tissue are stored at about 0° C. to about 40° C. The ophthalmic solution may be replaced on either a continuous basis or batch exchanged. The volume of ophthalmic solution per individual cornea being preserved would be from about 50 ml to about 500 ml.

34 Claims, No Drawings

USE OF OPHTHALMIC COMPOSITIONS INCLUDING LUBRICANT, DETURGESCENT AGENT, AND GLYCOSAMINOGLYCAN

CROSS REFERENCES TO RELATED APPLICATIONS

This application is related to U.S. Pat. No. 7,820,639 patented Oct. 26, 2010, entitled "Ophthalmic Compositions Including Lubricant, Deturgescent Agent, and Glycosaminoglycan and Methods of Using the Same"; the entire contents of which are hereby incorporated herein by reference.

BACKGROUND OF THE INVENTION

Field of the Invention

The invention generally relates to ophthalmic compositions including a lubricant, a deturgescent agent, and a glycosaminoglycan as well as to methods of using such ophthalmic compositions.

Various compositions utilizing a glycosaminoglycan such as chondroitin sulfate are known. For example, U.S. Pat. No. 4,486,416 relates to a method of protecting both human and animal endothelial and epithelial cells which are subject to exposure to trauma, and more particularly to protecting endothelial and epithelial cells in anticipation of surgical trauma using chondroitin sulfate.

U.S. Patent Application Publication Nos. 2002/0081289 and 2003/0198630 relate to an ophthalmic medicament which contains in aqueous solution or suspension at least one carbohydrate, at least one amino acid, at least one electrolyte, a chondroitin sulfate, and optionally further customary excipients. The publications state that the ophthalmic medicament can be employed in a large number of eye diseases and in particular in accompaniment to corneal transplantation and in refractive corneal surgery.

SUMMARY OF THE INVENTION

In one aspect, an ophthalmic composition is provided that comprises glycerol in a concentration of from 0.1% to 5.0%, dextran in a concentration of from 0.1% to 10.0%, chondroitin sulfate in a concentration of from 0.1% to 5.0%, and water.

In another aspect, an ophthalmic composition is provided that consists essentially of glycerol in a concentration of from 0.1% to 5.0%, dextran in a concentration of from 1.0% to 10.0%, chondroitin sulfate in a concentration of from 0.1% to 5.0%, and water.

In a further aspect, an ophthalmic composition is provided that consists of glycerol in a concentration of from 0.1% to 5.0%, dextran in a concentration of from 1.0% to 10.0%, chondroitin sulfate in a concentration of from 0.1% to 5.0%, water, a buffer, and a tonicity modulating agent.

In yet a further aspect, an ophthalmic composition is provided that consists of glycerol in a concentration of from 0.1% to 5.0%, dextran in a concentration of from 1.0% to 10.0%, chondroitin sulfate in a concentration of from 0.1% to 5.0%, and water.

In yet another aspect, a method of treating corneal edema is provided. The method comprises administering to a cornea of a subject suffering from or susceptible to corneal edema an effective amount of an ophthalmic composition comprising glycerol in a concentration of from 0.1% to 5.0%, dextran in a concentration of from 1.0% to 10.0%, chondroitin sulfate in a concentration of from 0.1% to 5.0%, and water.

In another embodiment, the present invention is a method of preserving tissue, especially ophthalmic tissue, most especially corneal tissue, such as a cornea. This new use is an in vitro rather than the previously known in vivo uses of similar solutions. The method includes the steps of first providing a liquid composition including glycerol in a concentration of from 0.1% to 5.0%, dextran in a concentration of from 1.0% to 10.0%, chondroitin sulfate in a concentration of from 0.1% to 5.0%, and water; and then placing tissue to be preserved in the liquid composition. Preferably, the tissue to be preserved is ophthalmic tissue, more preferably corneal tissue, and most preferably a cornea. Preferably, the storage is at a temperature of about 0° C. to about 40° C. The method may include replenishing the liquid composition in which the tissue to be preserved is placed, by batch replenishment or by continuous replenishment. Preferably, the cornea is placed in a volume of from about 50 ml to about 500 ml of liquid composition. Preferably, the method further includes the step of subsequently implanting the tissue, most preferably a cornea, preserved in the liquid composition. Preferably, the liquid composition is an ophthalmic composition consisting essentially of: glycerol in a concentration of from 0.1% to 5.0%, dextran in a concentration of from 1.0% to 10.0%, chondroitin sulfate in a concentration of from 0.1% to 5.0%, and water. Preferably, the liquid composition is an ophthalmic composition and glycerol is present in a concentration of from 0.3% to 1.7%, dextran is present in a concentration of from 3.0% to 7.0%, and chondroitin sulfate is present in a concentration of from 0.5% to 4.5%. Preferably, the liquid composition is an ophthalmic composition and glycerol is present in a concentration of from 0.6% to 1.4%, dextran is present in a concentration of from 4.0% to 6.0%, and chondroitin sulfate is present in a concentration of from 1.5% to 3.5%. Preferably, the liquid composition is an ophthalmic composition and glycerol is present in a concentration of from 0.8% to 1.2%, dextran is present in a concentration of from 4.5% to 5.5%, and chondroitin sulfate is present in a concentration of from 2.0% to 3.0%. Preferably, the liquid composition is an ophthalmic composition and chondroitin sulfate is present in a concentration of from 2.3% to 2.7%. Preferably, the liquid composition is an ophthalmic composition and glycerol is present in a concentration of 1.0%, dextran is present in a concentration of 5.0%, and chondroitin sulfate is present in a concentration of 2.5%. Preferably, the liquid composition is an ophthalmic composition consisting essentially of: glycerol in a concentration of from 0.1% to 5.0%, dextran in a concentration of from 1.0% to 10.0%, chondroitin sulfate in a concentration of from 0.1% to 5.0%, water, a buffer, and pH 6 to 8. Preferably, the pH of the composition is from 7.0 to 7.4. Preferably, the liquid composition is an ophthalmic composition and glycerol is present in a concentration of from 0.3% to 1.7%, dextran is present in a concentration of from 3.0% to 7.0%, and chondroitin sulfate is present in a concentration of from 0.5% to 4.5%. Preferably, the liquid composition is an ophthalmic composition and glycerol is present in a concentration of from 0.6% to 1.4%, dextran is present in a concentration of from 4.0% to 6.0%, and chondroitin sulfate is present in a concentration of from 1.5% to 3.5%. Preferably, the liquid composition is an ophthalmic composition and glycerol is present in a concentration of from 0.8% to 1.2%, dextran is present in a concentration of from 4.5% to 5.5%, and chondroitin sulfate is present in a concentration of from 2.0% to 3.0%. Preferably, the liquid composition is an ophthalmic composition and chondroitin sulfate is present in a concentration of from 2.3% to 2.7%. Preferably, the liquid composition is an ophthalmic composition and glycerol is present in a concentration of 1.0%, dextran is present in a concentration of 5.0%, and chondroitin sulfate is present in a concentration of 2.5%. Preferably, the liquid composition is an ophthalmic composition and the buffer is sodium borate and boric acid. Preferably, the liquid composition is an ophthalmic composition consisting of glycerol in a concentration of from 0.1% to 5.0%, dextran in a concentration of from 1.0% to 10.0%, chondroitin sulfate in a concentration of from 0.1% to 5.0%, and water. Preferably, the liquid composition is an ophthalmic composition and glycerol is present in a concentration of from 0.3% to 1.7%, dextran is present in a concentration of from 3.0% to 7.0%, and chondroitin sulfate is present in a concentration of from 0.5% to 4.5%. Preferably, the liquid composition is an ophthalmic composition and glycerol is present in a concentration of from 0.6% to 1.4%, dextran is present in a concentration of from 4.0% to 6.0%, and chondroitin sulfate is present in a concentration of from 1.5% to 3.5%. Preferably, the liquid composition is an ophthalmic composition and glycerol is present in a concentration of from 0.8% to 1.2%, dextran is present in a concentration of from 4.5% to 5.5%, and chondroitin sulfate is present in a concentration of from 2.0% to 3.0%. Preferably, the liquid composition is an ophthalmic composition and chondroitin sulfate is present in a concentration of from 2.3% to 2.7%. Preferably, the liquid composition is an ophthalmic composition and glycerol is present in a concentration of 1.0%, dextran is present in a concentration of 5.0%, and chondroitin sulfate is present in a concentration of 2.5%. Optionally, but preferably, the new solution might include mannitol at a concentration from about 0.01% to about 20%, most preferably at about 0.5%.

DETAILED DESCRIPTION OF THE PREFERRED EMBODIMENTS

The present invention relates to ophthalmic compositions as well as methods of using the same.

The ophthalmic compositions of the present invention comprise a lubricant, a deturgescent agent, a glycosaminoglycan, and water. The lubricant is preferably glycerol, although other lubricants may be used, including, but not limited to, hydroxypropyl methylcellulose, carboxypropyl methylcellulose, sorbitol, polyvinyl pyrrolidone, polyethylene glycol, polyvinyl acetate, and combinations thereof.

The deturgescent agent is preferably dextran, although other deturgescent agents may be used including, but not limited to, dextran sulfate, NaCl, dextrose, sucrose, other sugars, and combinations thereof. Any suitable molecular weight dextran or mixture thereof may be used, including dextran 40, dextran 70, and/or dextran 500.

The glycosaminoglycan is preferably chondroitin sulfate, although other glycosaminoglycans (or other protective coating agents) may be used including, but not limited to, chondroitin, dermatan sulfate, dermatin sulfate, heparin sulfate, heparan sulfate, keratin sulfate, keratan sulfate, hyaluronic acid, and mixtures thereof. Any one isomer or salt of the glycosaminoglycan may be used, or a mixture of isomers and/or salts of the glycosaminoglycan may be used. For example, as used herein, "chondroitin sulfate" includes any type of chondroitin sulfate, including isomers and salts thereof as well as mixtures of isomers and/or salts thereof.

In some embodiments, the ophthalmic composition consists essentially of a lubricant, a deturgescent agent, a glycosaminoglycan, and water. The compositions may also include a buffer (e.g., buffers including citrates, phosphates, borates, bicarbonates, sodium salts, potassium salts, etc.), an acid or base to modify pH, a tonicity modulating agent (e.g., NaCl), and/or an antioxidant/free radical scavenger (e.g., ascorbate, ascorbic acid, glutathione, etc.). In other embodiments, the ophthalmic compositions consist of a lubricant, a deturgescent agent, a glycosaminoglycan, water, a buffer, and a tonicity modulating agent. In yet other embodiments, the ophthalmic compositions consist of a lubricant, a deturgescent agent, a glycosaminoglycan, and water.

The ophthalmic composition typically comprises an aqueous solution including a lubricant in a concentration of from 0.05% to 10.0%, a deturgescent agent in a concentration of from 0.1% to 20%, a glycosaminoglycan in a concentration of from 0.05% to 10.0%, and water (as used herein, "concentration" of a component of an ophthalmic composition means concentration based on mass of the component per total volume of the composition (i.e., mg/100 mL), and is typically expressed as a percentage).

In a preferred embodiment, the ophthalmic composition includes glycerol, dextran, chondroitin sulfate, and water. The glycerol is typically present in such a composition in a concentration of from 0.1% to 5.0%, preferably from 0.3% to 1.7%, more preferably from 0.6% to 1.4%, even more preferably from 0.8% to 1.2%, and even more preferably in a concentration of 1.0%. Dextran is typically present in such a composition in a concentration of from 0.1% to 10%, preferably from 0.5% to 10%, more preferably from 1.0% to 10.0%, more preferably from 3% to 7%, even more preferably from 4% to 6%, yet even more preferably from 4.5% to 5.5%, and even more preferably in a concentration of 5.0%. Chondroitin sulfate is typically present in such a composition in a concentration of from 0.1% to 5.0%, preferably from 0.5% to 4.5%, more preferably from 1.5% to 3.5%, even more preferably from 2.0% to 3.0%, even more preferably 2.3% to 2.7%, and even more preferably in a concentration of 2.5%.

The ophthalmic compositions typically have a pH from 5.0 to 9.0, preferably from 6.0 to 8.0, more preferably from 7.0 to 7.4, and even more preferably 7.0, although the compositions may also have a pH outside of these ranges. A buffer (e.g., a buffer with intrinsic antimicrobial properties such as a sodium borate/boric acid buffer) may be used to achieve (and maintain) the desired pH of the compositions, and/or an acid or base may be added to adjust the pH of the compositions to the desired level. Buffers that do not require adjustment of the pH of the compositions with additional acid or base are preferred.

The ophthalmic compositions typically have an osmolarity of from 100 to 500 milliosmoles/liter (mOsm/L), preferably from 150 to 450 mOsm/L, and more preferably from 200 to 400 mOsm/L, although the compositions may also have an osmolarity outside of these ranges. As mentioned above, a tonicity modulating agent such as sodium chloride may also be used in the compositions.

As stated above, in some embodiments, the ophthalmic composition comprises glycerol, dextran, chondroitin sulfate, and water, and optionally includes a buffer, an acid or base, a tonicity modulating agent, and/or a free radical scavenger. In other embodiments, the ophthalmic composition consists essentially of glycerol, dextran, chondroitin sulfate, and water, and optionally includes a buffer, an acid or base, a tonicity modulating agent, and/or a free radical scavenger. In further embodiments, the composition consists of glycerol, dextran, chondroitin sulfate, and water, and optionally includes a buffer, an acid or base, a tonicity modulating agent, and/or a free radical scavenger. In yet other embodiments, the composition consists of glycerol, dextran, chondroitin sulfate, and water.

In one particularly preferred embodiment, the ophthalmic composition comprises glycerol in a concentration of from 0.1% to 5.0%, dextran in a concentration of from 1.0% to 10.0%, chondroitin sulfate in a concentration of from 0.1% to 5.0%, and water, and optionally includes a buffer, an acid or base, a tonicity modulating agent, and/or a free radical scavenger. The pH of such a composition is preferably from 6.0 to 8.0.

In another preferred embodiment, the ophthalmic composition consists essentially of glycerol in a concentration of from 0.1% to 5.0%, dextran in a concentration of from 1.0% to 10.0%, chondroitin sulfate in a concentration of from 0.1% to 5.0%, and water, and optionally includes a buffer, an acid or base, a tonicity modulating agent, and/or a free radical scavenger. The pH of such a composition is preferably from 6.0 to 8.0.

In yet another preferred embodiment, the ophthalmic composition consists of glycerol in a concentration of from 0.1% to 5.0%, dextran in a concentration of from 1.0% to 10.0%, chondroitin sulfate in a concentration of from 0.1% to 5.0%, water, a buffer, and a tonicity modulating agent. The pH of such a composition is preferably from 6.0 to 8.0.

In yet a further preferred embodiment, the ophthalmic composition consists of glycerol in a concentration of from 0.1% to 5.0%, dextran in a concentration of from 1.0% to 10.0%, chondroitin sulfate in a concentration of from 0.1% to 5.0%, and water. The pH of such a composition is preferably from 6.0 to 8.0.

The ophthalmic compositions are useful for preventative and therapeutic treatment of numerous ocular conditions and diseases as well as before, during, and after various ocular surgeries, as the compositions provide for ocular surface lubrication, cell membrane stabilization, corneal deturgescence, and, when the ophthalmic compositions contain an antioxidant/free radical scavenger, antioxidant activity. The ophthalmic compositions are useful for protecting the ocular surface (e.g., cornea and conjunctiva), corneal epithelial cells, corneal endothelial cells, and/or other ocular tissues during surgery on an eye. In addition to preventing damage to such ocular tissues during surgery, the ophthalmic compositions may be useful in wound healing after surgery or other events causing injury to the eye. The ophthalmic compositions may also be useful for reducing corneal edema (e.g., during and after corneal transplantation surgery) as well as maintaining corneal deturgescence. The ophthalmic compositions may further be used as a general surgical rinsing solution, especially during ocular surgeries. In addition, the ophthalmic compositions may be useful for rehabilitating stressed or damaged ocular tissue (e.g., an ocular surface) to a normal state (i.e., homeostasis). For example, the ophthalmic compositions may be useful for rehabilitating the ocular surface before and after contact lens wear. Furthermore, the ophthalmic compositions may be useful for maintaining ocular tissue (e.g., an ocular surface) at a normal state (i.e., homeostasis). The ophthalmic compositions may also be useful for enhancing comfort during contact lens wear.

Methods of protecting an animal (e.g., a mammal, especially a human) ocular surface, cornea, corneal epithelial cells, corneal endothelial cells, and/or other ocular tissue comprise administering an effective amount of an ophthalmic composition described herein to the ocular surface, cornea, corneal epithelial cells, corneal endothelial cells, and/or other ocular tissue of a subject. Such administration may occur before and/or during events such as surgery that may cause trauma to the ocular surface, cornea, corneal epithelial cells, corneal endothelial cells, and/or other ocular tissue. The ophthalmic composition preferably maintains contact with the ocular surface, cornea, corneal epithelial cells, corneal endothelial cells, and/or other ocular tissue during the trauma causing event (e.g., surgery).

Methods of treating wounds and/or promoting healing after events causing trauma to an animal (e.g., a mammal, especially a human) ocular surface, cornea, corneal epithelial cells, corneal endothelial cells, and/or other ocular tissue comprise administering an effective amount of an ophthalmic composition described herein to the ocular surface, cornea, corneal epithelial cells, corneal endothelial cells, and/or other ocular tissue of a subject. Such administration may occur before, during, or after events such as surgery that may cause trauma to such ocular tissues, and the ophthalmic composition preferably maintains contact with such ocular tissues after the trauma causing event (e.g., ocular surgery).

Methods of reducing corneal edema comprise administering an effective amount of an ophthalmic composition described herein to an animal (e.g., a mammal, especially a human) cornea of a subject suffering from or susceptible to corneal edema in order to reduce and/or prevent edema in the cornea. Such corneal edema may be caused by an event or disease causing corneal edema such as, for example, corneal transplantation surgery or corneal edema occurring spontaneously. The ophthalmic composition may be administered to the cornea before and/or after edema occurs (e.g., before, during, and/or after corneal transplantation surgery) in order to reduce and/or prevent corneal edema resulting from events such as surgery anticipated to cause such edema.

Methods of rehabilitating stressed or damaged ocular tissue (e.g., an ocular surface) to a normal state (i.e., homeostasis) comprise administering an effective amount of an ophthalmic composition described herein to the stressed or damaged ocular tissue (e.g., ocular surface). In such methods, the stressed or damaged ocular tissue (e.g., ocular surface) is preferably fully rehabilitated, although the ocular tissue may only be partially rehabilitated. Stressed or damaged ocular tissue conditions that may be treated with the ophthalmic compositions include, but are not limited to, dry eye, swollen ocular tissue, excess free radicals, or other conditions stressing or damaging ocular tissue. For example, such a method could be used before and/or after contact lens wear of a subject in order to rehabilitate the ocular surface.

Methods of maintaining ocular tissue (e.g., an ocular surface) at a normal state (i.e., homeostasis) comprise administering an effective amount of an ophthalmic composition described herein to the ocular tissue (e.g., ocular surface). Such a method may be used before, during, or after stress or other damage to the ocular tissue (e.g., ocular surface) such as before, during, and after contact lens wear.

Methods of enhancing comfort during contact lens wear comprise administering an effective amount of an ophthalmic composition described herein to the ocular surface and/or other ocular tissue of a subject wearing one or more contact lenses.

The ophthalmic solutions may be administered as a single dosage, in periodic applications, or may be maintained on the ophthalmic tissue continuously or substantially continuously as appropriate for the particular use. For example, the ophthalmic compositions may be administered once per day in some embodiments, may be administered once every minute for a period of 5 to 10 minutes in other embodiments, and may be administered more or less frequently in yet other embodiments. For methods of maintaining ocular tissue at a normal state as well as in other embodiments of methods of rehabilitating stressed or damaged ocular tissue, an effective amount of the ophthalmic compositions may be applied between 1 to 16 times a day (e.g., from 1 to 8 times a day, from 1 to 6 times a day, or from 1 to 4 times a day), although the ophthalmic compositions may be administered more or less frequently in methods of maintaining ocular tissue as well as in other methods. As will be understood, an effective amount of ophthalmic composition will vary depending upon the particular use, the particular patient and eye the composition is being applied to, and other variable factors. For example, for methods of rehabilitating stressed or damaged ocular tissue, two or three drops of the ophthalmic composition may be used immediately after an insult and could be administered every minute (or other interval) for a period thereafter, although other amounts of ophthalmic compositions could be used in more or less frequency.

Any effective method may be used to produce the ophthalmic compositions described herein. An example of a method for making an ophthalmic composition using a borate buffer follows:

1. Add to the manufacturing vessel 80% of the batch quantity of Purified Water.
2. Heat to 85-90 degree C.
3. While mixing, add the batch quantity of Dextran-40K. Make sure powder is not splashed on vessel wall above the water level.
4. Mix until all Dextran is dissolved and a clear solution is observed.
5. Discontinue heating and allow solution to start cooling.
6. While cooling, increase speed of mixer and add slowly and to vortex the batch quantity of Chondroitin Sulfate Sodium. Avoid formation of undissolved lumps. Mix until all is dissolved.
7. Add batch quantity of Glycerol. Rinse container with few milliliters of Purified Water and add to the manufacturing vessel to assure complete transfer of glycerol.
8. Add batch quantity of Boric Acid. Mix to dissolve.
9. Add batch quantity of Sodium Borate (decahydrate). Mix to dissolve.
10. Qs with Purified Water. Mix to homogeneity.
11. Using appropriate filters (e.g. 5 to 25 micron filters) filter the solution to remove any undissolved particles.
12. Sterile filter through 0.20 micron filters.

MODE OF OPERATION

The invention will be further explained by the following illustrative examples that are intended to be non-limiting.

Example 1

Four different formulations of the ophthalmic compositions described herein were prepared and the comfort of such formulations was compared to Systane® lubricant eye drops, which contain polyethylene glycol 400, propylene glycol, and HP-guar. The four formulations of the ophthalmic compositions (designated as Cla-022, Cla-026, Cla-028, and Cla-030) that were prepared are listed below in Table I:

TABLE I

|  | Cla-022 | Cla-026 | Cla-028 | Cla-030 |
| --- | --- | --- | --- | --- |
| Glycerol (percent, weight/volume) | 1.0 | 1.0 | 1.0 | 1.0 |
| Chondroitin sulfate (percent, weight/volume) | 2.5 | 2.5 | 2.5 | 2.5 |
| Dextran, 40,000 (percent, weight/volume) | 5.0 | 5.0 | 2.5 | 1.0 |
| Boric Acid (percent, weight/volume) | 0.5 | 0.5 | 0.5 | 0.5 |
| Sodium borate (percent, weight/volume) | 0.18 | 0.18 | 0.18 | 0.18 |
| Sodium chloride (percent, weight/volume) | 0 | 0.25 | 0.25 | 0.25 |
| Purified water | balance | balance | balance | balance |

Four blinded tests were conducted in order to compare the comfort level of the different test formulations to the comfort of Systane®. lubricant eye drops. In each test, the Systane®. lubricant eye drops were tested against one of the four formulations. At three time points over a 24 hour period (8 am, 12 pm, and 5 pm), each human subject received one drop of one of the two compositions in the right eye and received a drop of the other composition in the left eye, but the subjects were not informed of the identity of the compositions. The composition administered to each eye remained constant during the test period (i.e., the same composition was applied to the same eye at each time point of application). At various time points discussed below, the subject indicated the comfort of each eye on a scale of 1-10, with 10 being the most comfortable. The subject gave comfort ratings at each of the following time points:

| Day 1 | |
| --- | --- |
| 8 am | (1) immediately upon administration, and |
|  | (2) two minutes after administration; |
| Noon | (1) pre-administration, |
|  | (2) immediately upon administration, and |
|  | (3) two minutes after administration; |
| 5 pm | (1) pre-administration, |
|  | (2) immediately upon administration, and |
|  | (3) two minutes after administration; |
| Bedtime | (1) at bedtime for subject; |
| Day 2 | |
| 8 am | (1) at 8 am. |

The results of each of the four tests on the comfort of the formulations (Cla-022, Cla-026, Cla-028, Cla-030) as compared to Systane® lubricant eye drops (Sys) are shown below in Tables II-V.

TABLE IIa

| Cla-022 v. Systane: Day 1, 8 am-12 pm | | | | | | | | | | |
| --- | --- | --- | --- | --- | --- | --- | --- | --- | --- | --- |
| | 8 am-admin. | | 8 am-2 min. after admin. | | 12 pm Pre-admin. | | 12 pm- Admin | | 12 pm-2 min. after admin. | |
| Subject | Sys | Cla-022 | Sys | Cla-022 | Sys | Cla-022 | Sys | Cla-022 | Sys | Cla-022 |
| A | 10 | 10 | 9 | 10 | 5 | 6 | 8 | 8 | 8 | 8 |
| B | 8 | 6 | 5 | 7 | 8 | 8 | 9 | 6 | 7 | 7 |
| C | 9 | 6 | 9 | 6 | 9 | 7 | 9 | 7 | 8 | 8 |
| D | 10 | 9 | 10 | 9 | 10 | 10 | 8 | 10 | 10 | 9 |
| E | 10 | 10 | 9 | 10 | 10 | 10 | 10 | 10 | 9 | 9 |
| F | 9 | 9 | 9 | 9 | 10 | 10 | 9 | 9 | 9 | 9 |

TABLE IIa-continued

Cla-022 v. Systane: Day 1, 8 am-12 pm

| Subject | 8 am-admin. | | 8 am-2 min. after admin. | | 12 pm Pre-admin. | | 12 pm-Admin | | 12 pm-2 min. after admin. | |
|---|---|---|---|---|---|---|---|---|---|---|
| | Sys | Cla-022 | Sys | Cla-022 | Sys | Cla-022 | Sys | Cla-022 | Sys | Cla-022 |
| G | 8 | 3 | 8 | 6 | 7 | 8 | 2 | 8 | 4 | 8 |
| H | 9 | 9 | 9 | 9 | 10 | 10 | 9 | 10 | 9 | 9 |
| I | 9 | 7 | 9 | 4 | 7 | 8 | 6 | 5 | 6 | 6 |
| J | 9 | 9 | 9 | 9 | 10 | 10 | 10 | 7 | 10 | 9 |
| K | 10 | 8 | 10 | 9 | 9 | 9 | 8 | 8 | 9 | 9 |
| L | 8 | 7 | 9 | 9 | 8 | 8 | 8 | 7 | 8 | 7 |
| M | 8 | 6 | 8 | 6 | 8 | 8 | 7 | 6 | 7 | 6 |
| N | 9 | 9 | 7 | 9 | 9 | 9 | 8 | 8 | 7 | 9 |
| Avg Score | 9.0000 | 7.7143 | 8.5714 | 8.0000 | 8.5714 | 8.6429 | 7.9286 | 7.7857 | 7.9286 | 8.0714 |

TABLE IIb

Cla-022 v. Systane: Day 1, 5 pm-Day 2, 8 am

| Subject | 5 pm-Pre-admin. | | 5 pm-Admin. | | 5 pm-2 min. after admin. | | Bedtime | | Day 2-8 am. | |
|---|---|---|---|---|---|---|---|---|---|---|
| | Sys | Cla-022 | Sys | Cla-022 | Sys | Cla-022 | Sys | Cla-022 | Sys | Cla-022 |
| A | 6 | 5 | 7 | 7 | 7 | 7 | 7 | 7 | 7 | 7 |
| B | 2 | 3 | 5 | 7 | 8 | 8 | 3 | 3 | 5 | 5 |
| C | 9 | 9 | 9 | 9 | 9 | 9 | 9 | 9 | 9 | 9 |
| D | 10 | 10 | 10 | 7 | 10 | 7 | 9 | 9 | 9 | 8 |
| E | 9 | 8 | 9 | 8 | 8 | 8 | 10 | 10 | 10 | 10 |
| F | 9 | 9 | 8 | 7 | 9 | 9 | 9 | 9 | 10 | 10 |
| G | 5 | 9 | 8 | 2 | 8 | 3 | 9 | 9 | 9 | 4 |
| H | 10 | 10 | 10 | 9 | 9 | 10 | 10 | 10 | 10 | 10 |
| I | 6 | 7 | 5.5 | 6.5 | 6 | 6.5 | 7 | 8 | 8 | 8 |
| J | 10 | 10 | 10 | 10 | 10 | 10 | 10 | 10 | 10 | 10 |
| K | 8 | 8 | 8 | 8 | 9 | 9 | 9 | 9 | 9 | 9 |
| L | 7 | 7 | 8 | 7 | 8 | 8 | 8 | 8 | 8 | 8 |
| M | 7 | 7 | 8 | 6 | 8 | 6 | 7 | 7 | 7 | 7 |
| N | 8 | 8 | 8 | 8 | 6 | 8 | 8 | 8 | 8 | 8 |
| Avg Score | 7.5714 | 7.8571 | 8.1071 | 7.2500 | 8.2143 | 7.7500 | 8.2143 | 8.2857 | 8.5000 | 8.0714 |

TABLE IIIa

Cla-026 v. Systane: Day 1, 8 am-12 pm

| Subject | 8 am-admin. | | 8 am-2 min. after admin. | | 12 pm Pre-admin. | | 12 pm-Admin. | | 12 pm-2 min. after admin. | |
|---|---|---|---|---|---|---|---|---|---|---|
| | Sys | Cla-026 | Sys | Cla-026 | Sys | Cla-026 | Sys | Cla-026 | Sys | Cla-026 |
| A | 10 | 10 | 10 | 10 | 7 | 7 | 10 | 10 | 10 | 10 |
| B | 10 | 7 | 8 | 6 | 10 | 7 | 6 | 4 | 3 | 7 |
| C | 7 | 7 | 9 | 8 | 6 | 6 | 7 | 7 | 9 | 9 |
| D | 9 | 9 | 10 | 10 | 10 | 10 | 10 | 10 | 10 | 10 |
| E | 10 | 10 | 8 | 9 | 9 | 9 | 9 | 9 | 8 | 8 |
| F | 9 | 9 | 9 | 9 | 10 | 10 | 6 | 8 | 9 | 9 |
| G | 7 | 4 | 3 | 8 | 8 | 5 | 7 | 3 | 3 | 8 |
| H | 10 | 10 | 10 | 10 | 10 | 10 | 10 | 9 | 10 | 9 |
| I | 7 | 8 | 7.5 | 7.5 | 8 | 7 | 7 | 7 | 7 | 6 |
| J | 10 | 10 | 7 | 8 | 8 | 10 | 9 | 10 | 9 | 9 |
| K | 8 | 9 | 9 | 9 | 9 | 9 | 8 | 8 | 9 | 9 |
| L | 8 | 8 | 9 | 9 | 8 | 8 | 9 | 9 | 9 | 9 |
| M | 7 | 8 | 6 | 7 | 6 | 7 | 7 | 7 | 6 | 6 |
| N | 10 | 9 | 10 | 8 | 10 | 9 | 10 | 7 | 10 | 5 |
| Avg Score | 8.7143 | 8.4286 | 8.2500 | 8.4643 | 8.5000 | 8.1429 | 8.2143 | 7.7143 | 8.0000 | 8.1429 |

TABLE IIIb

Cla-026 v. Systane: Day 1, 5 pm-Day 2, 8 am

| Subject | 5 pm-Pre-admin. | | 5 pm-Admin. | | 5 pm-2 min. after admin. | | Bedtime | | Day 2-8 am | |
|---|---|---|---|---|---|---|---|---|---|---|
| | Sys | Cla-026 | Sys | Cla-026 | Sys | Cla-026 | Sys | Cla-026 | Sys | Cla-026 |
| A | 6 | 6 | 10 | 10 | 9 | 10 | 9 | 9 | 7 | 7 |
| B | 1 | 2 | 4 | 3 | 3 | 5 | 3 | 3 | 5 | 5 |
| C | 7 | 7 | 8 | 9 | 9 | 9 | 6 | 6 | 8 | 8 |
| D | 10 | 10 | 10 | 10 | 10 | 10 | 10 | 10 | 10 | 10 |
| E | 9 | 10 | 8 | 9 | 10 | 9 | 9 | 9 | 10 | 10 |
| F | 8 | 8 | 9 | 9 | 9 | 9 | | | | |
| G | 7 | 9 | 7 | 4 | 3 | 8 | 8 | 8 | 10 | 10 |
| I-1 | 10 | 10 | 10 | 10 | 10 | 10 | 10 | 10 | 10 | 10 |
| I | 6.5 | 6 | 6 | 5 | 6 | 4 | 8 | 8 | 8 | 8 |
| J | 8 | 9 | 9 | 9 | 8 | 9 | 8 | 7 | 9 | 9 |
| K | 9 | 9 | 9 | 9 | 9 | 9 | 9 | 9 | 9 | 9 |
| L | 7 | 7 | 8 | 8 | 8 | 8 | 8 | 8 | 8 | 8 |
| M | 5 | 5 | 7 | 8 | 7 | 7 | 7 | 8 | 7 | 8 |
| N | 8 | 8 | 8 | 7 | 8 | 5 | 8 | 6 | 9 | 9 |
| Avg Score | 7.2500 | 7.5714 | 8.0714 | 7.8571 | 7.7857 | 8.0000 | 7.3571 | 7.2143 | 7.8571 | 7.9286 |

TABLE IVa

Cla-028 v. Systane: Day 1, 8 am-12 pm

| Subject | 8 am-2 min. | | 8 am-admin. after admin. | | 12 pm Pre-admin. | | 12 pm-Admin | | 12 pm-2 min. after admin. | |
|---|---|---|---|---|---|---|---|---|---|---|
| | Sys | Cla-028 | Sys | Cla-028 | Sys | Cla-028 | Sys | Cla-028 | Sys | Cla-028 |
| A | 10 | 10 | 10 | 10 | 10 | 6 | 9 | 9 | 9 | 9 |
| B | 9 | 7 | 9 | 7 | 10 | 7 | 6 | 8 | 5 | 9 |
| C | 8 | 7 | 7 | 6 | 8 | 8 | 7 | 7 | 8 | 8 |
| D | 10 | 9 | 10 | 10 | 10 | 10 | 10 | 10 | 10 | 10 |
| E | 10 | 8 | 10 | 8 | 10 | 10 | 10 | 10 | 8 | 9 |
| F | 6 | 7 | 8 | 9 | 9 | 9 | 6 | 6 | 8 | 8 |
| G | 8 | 8 | 6 | 8 | 10 | 10 | 8 | 8 | 8 | 5 |
| H | 10 | 10 | 9 | 9 | 10 | 10 | 10 | 10 | 9 | 10 |
| I | 8 | 8 | 8 | 7 | 10 | 10 | 9 | 10 | 9.5 | 9.5 |
| J | 10 | 9 | 9 | 9 | 8 | 5 | 9 | 9 | 9 | 7 |
| K | 8 | 8 | 8 | 8 | 10 | 10 | 8 | 8 | 9 | 9 |
| L | 10 | 10 | 10 | 10 | 8 | 8 | 10 | 9 | 10 | 9 |
| M | 9 | 9 | 9 | 8 | 9 | 9 | 9 | 8 | 9 | 8 |
| N | 10 | 10 | 10 | 7 | 10 | 10 | 10 | 10 | 10 | 7 |
| Avg Score | 9.0000 | 8.5714 | 8.7857 | 8.2857 | 9.4286 | 8.7143 | 8.6429 | 8.7143 | 8.6786 | 8.3929 |

TABLE IVb

Cla-028 v. Systane: Day 1, 5 pm-Day 2, 8 am

| Subject | 5 pm-Pre-admin. | | 5 pm-Admin. | | 5 pm-2 min. after admin. | | Bedtime | | Day 2-8 am | |
|---|---|---|---|---|---|---|---|---|---|---|
| | Sys | Cla-028 | Sys | Cla-028 | Sys | Cla-028 | Sys | Cla-028 | Sys | Cla-028 |
| A | 6 | 6 | 9 | 9 | 8 | 8 | 8 | 8 | 7 | 7 |
| B | 8 | 10 | 5 | 6 | 6 | 8 | 10 | 10 | 10 | 10 |
| C | 8 | 8 | 8 | 7 | 9 | 7 | 8 | 8 | 8 | 7 |
| D | 10 | 10 | 9 | 9 | 10 | 10 | 10 | 10 | 9 | 9 |
| E | 10 | 10 | 10 | 10 | 9 | 8 | 9 | 9 | 10 | 10 |
| F | 10 | 10 | 8 | 8 | 9 | 9 | 9 | 9 | 9 | 9 |
| G | 10 | 10 | 8 | 6 | 9 | 8 | 10 | 10 | 10 | 10 |
| H | 10 | 10 | 10 | 10 | 10 | 10 | 10 | 10 | 10 | 10 |

TABLE IVb-continued

Cla-028 v. Systane: Day 1, 5 pm-Day 2, 8 am

| Subject | 5 pm-Pre-admin. | | 5 pm-Admin. | | 5 pm-2 min. after admin. | | Bedtime | | Day 2-8 am | |
|---|---|---|---|---|---|---|---|---|---|---|
| | Sys | Cla-028 | Sys | Cla-028 | Sys | Cla-028 | Sys | Cla-028 | Sys | Cla-028 |
| I | 8 | 8 | 9 | 9 | 8 | 8 | 8 | 8 | 10 | 10 |
| J | 8 | 7 | 10 | 9 | 9 | 8 | 6 | 4 | 9 | 8 |
| K | 9 | 9 | 8 | 8. | 9 | 9 | 8 | 8 | 9 | 9 |
| L | 8 | 8 | 8 | 8 | 9 | 9 | 8 | 8 | 8 | 8 |
| M | 9 | 9 | 9 | 9 | 8 | 8 | 8 | 8 | 8 | 8 |
| N | 10 | 10 | 10 | 8 | 9 | 8 | 10 | 10 | 10 | 10 |
| Avg Score | 8.8571 | 8.9286 | 8.6429 | 8.2857 | 8.7143 | 8.4286 | 8.7143 | 8.5714 | 9.0714 | 8.9286 |

TABLE Va

Cla-030 v. Systane: Day 1, 8 am-12 pm

| Subject | 8 am-admin. | | 8 am-2 min. after admin. | | 12 pm Pre-admin. | | 12 pm-Admin | | 12 pm-2 min. after admin. | |
|---|---|---|---|---|---|---|---|---|---|---|
| | Sys | Cla-030 | Sys | Cla-030 | Sys | Cla-030 | Sys | Cla-030 | Sys | Cla-030 |
| A | 10 | 10 | 10 | 10 | 8 | 7 | 10 | 9 | 9 | 10 |
| B | 9 | 5 | 9 | 9 | 9 | 8 | 9 | 9 | 10 | 10 |
| C | 7 | 9 | 8 | 9 | 6 | 9 | 7 | 7 | 9 | 9 |
| D | 9 | 10 | 10 | 10 | 9 | 9 | 10 | 9 | 10 | 9 |
| E | 10 | 10 | 9 | 9 | 10 | 10 | 10 | 10 | 9 | 9 |
| F | 7 | 7 | 9 | 9 | 9 | 9 | 8 | 8 | 9 | 9 |
| G | 8 | 6 | 6 | 8 | 10 | 10 | 7 | 7 | 8 | 8 |
| H | 10 | 9 | 10 | 9 | 10 | 10 | 10 | 10 | 8 | 10 |
| I | 7 | 7.5 | 7 | 9 | 9 | 9 | 8 | 7 | 8 | 8 |
| J | 10 | 10 | 10 | 9 | 7 | 8 | 10 | 6 | 10 | 8 |
| K | 9 | 9 | 8 | 8 | 9 | 9 | 9 | 9 | 9 | 9 |
| L | 7 | 7 | 9 | 9 | 8 | 8 | 8 | 8 | 8 | 8 |
| M | 8. | 7 | 8 | 7 | 7 | 7 | 8 | 8 | 7 | 7 |
| N | 10 | 10 | 10 | 10 | 10 | 10 | 10 | 10 | 10 | 9.5 |
| Avg Score | 8.6429 | 8.3214 | 8.7857 | 8.9286 | 8.6429 | 8.7857 | 8.8571 | 8.3571 | 8.8571 | 8.8214 |

TABLE Vb

Cla-030 v. Systane: Day 1, 5 pm-Day 2, 8 am

| Subject | 5 pm-Pre-admin. | | 5 pm-Admin. | | 5 pm-2 min. after admin. | | Bedtime | | Day 2-8 am | |
|---|---|---|---|---|---|---|---|---|---|---|
| | Sys | Cla-030 | Sys | Cla-030 | Sys | Cla-030 | Sys | Cla-030 | Sys | Cla-030 |
| A | 8 | 8 | 10 | 10 | 9 | 9 | 9 | 9 | 8 | 8 |
| B | 7 | 10 | 9 | 7 | 9 | 7 | 9 | 5 | 10 | 7 |
| C | 7 | 7 | 7 | 7 | 9 | 9 | 7 | 7 | 9 | 9 |
| D | 9 | 9 | 9 | 10 | 10 | 10 | 9 | 9 | 8 | 8 |
| E | 9 | 9 | 9 | 9 | 9 | 9 | 9 | 9 | 10 | 10 |
| F | 10 | 10 | 9 | 9 | 10 | 10 | 9 | 9 | 9 | 9 |
| G | 10 | 10 | 8 | 6 | 9 | 8 | 2 | 5 | 4 | 8 |
| H | 10 | 10 | 8 | 10 | 10 | 10 | 10 | 10 | 10 | 10 |
| I | 7 | 7 | 6.5 | 7 | 6.5 | 7 | 9 | 9 | 10 | 10 |
| J | 8 | 8 | 10 | 7 | 9 | 8 | 6 | 3 | 9 | 8 |
| K | 9 | 9 | 9 | 9 | 9 | 9 | 8 | 8 | 9 | 9 |
| L | 6 | 7 | 7 | 7 | 7 | 7 | 8 | 8 | 8 | 8 |
| M | 6 | 7 | 8 | 8 | 8 | 7 | 6 | 7 | 6 | 7 |
| N | 10 | 10 | 8 | 8 | 7 | 7 | 9 | 9 | 9 | 9 |
| Avg Score | 8.2857 | 8.6429 | 8.3929 | 8.1429 | 8.6786 | 8.3571 | 7.8571 | 7.6429 | 8.5000 | 8.5714 |

Example 2

One unbuffered formulation, one phosphate buffered formulation, and one borate buffered formulation of the ophthalmic compositions described herein were prepared as described in Table VI below. The borate buffered formulation did not require any pH adjustment, as its natural pH was 7.4.

TABLE VI

| Ingredient | Unbuffered Solution Percent (wt/vol) | Borate Buffer Percent (wt/vol) | Phosphate Buffer Percent (wt/vol) |
|---|---|---|---|
| Glycerol | 1.0 | 1.0 | 1.0 |
| Chondroitin Sulfate | 2.5 | 2.5 | 2.5 |
| Dextran-40 | 5.0 | 5.0 | 5.0 |
| Sodium Chloride | 0.3 | — | 0.3 |
| NaOH or HCl | To adjust pH to 7.4 | None required | To adjust pH to 7.4 |
| Boric Acid | — | 0.5 | — |
| Sodium Borate | — | 0.18 | — |
| Phophate buffer 0.005M | — | — | q.s. to 100 |
| Purified Water | q.s. to 100 | q.s. to 100 | q.s. to 100 |

In order to evaluate the comfort of the solutions, blinded tests were conducted on a group of 16 human subjects. In each test, one drop of one of the buffered formulations was instilled in one eye of a subject and one drop of the unbuffered formulation was instilled in the contralateral eye of the subject. Comfort was evaluated immediately after instillation of the drops and 2 minutes post instillation; the subject indicated the comfort of each eye on a scale of 1-10, with 10 being the most comfortable. The study was repeated the next day using the other buffered formulation in one eye and the unbuffered formulation in the contralateral eye. Both study director and subjects were masked.

The average comfort scores for each of the formulations are shown in Table VII below:

TABLE VII

| Unbuffered Solution | | Borate Buffer | | Unbuffered Solution | | Phosphate Buffer | |
|---|---|---|---|---|---|---|---|
| Immediate | 2 min | Immediate | 2 min | Immediate | 2 min | Immediate | 2 min |
| 8.906 | 9.031 | 8.844 | 9.000 | 8.656 | 9.094 | 8.938 | 8.875 |

The preferred concentrations are the same as previously described for an ophthalmic solution that can be in contact with the cornea continuously. Such ophthalmic solution would also be compatible with corneal preservation and would be useful in corneal preservation or other ocular tissue preservation or any tissue preservation in an eye or tissue bank. The envisioned storage or preservation temperatures for in vitro storage or preservation of tissue, such as a cornea, would be from about 0° to about 40° Centigrade. Preferably, in one embodiment, a vial of solution at those temperatures could be changed or, alternatively, exchanged, during preservation if needed or desired, using from about 50 ml to about 500 ml for a cornea and appropriately larger volumes for other larger tissues and organs, such as kidneys. Appropriate structure might be included in the vial to easily retain tissue to be preserved within the vial while the solution is changed or exchanged. The solution might, in one embodiment, be batch exchanged every three to seven days. The change or exchange of solution might be either batchwise or continuous renewal of solution. The primary components of the composition are glycerol from about 0.10% to about 10.0% and possibly hydroxypropyl methylcellulose (HPMC) or, alternatively, carboxypropyl methylcellulose (CPMC) at concentrations from about 0.1% to about 5.0%. In one preferred embodiment, Optisol® 65, commercially available from Bausch & Lomb, Incorporated, is used as an intermediate, to which the glycerol and the HPMC or CPMC is added. Optionally, the solution for tissue preservation may also include mannitol at concentrations from about 0.01% to about 20%, preferably at about 0.5%. The preferred embodiment for glycerol is 1% and for HPMC/CPMC is 0.5%. Within the solution, the various components serve one or more functions. The glycerol serves as a lubricant, as an osmotic agent to enhance detergescence, and as in an osmoprotectant of tissue. The glycerol component will function to generate thinner corneas with healthier endothelium and epithelium and keratocytes. It will also reduce endothelial cell loss during the surgery by protecting the cells from mechanical damage, for example, during the passage of a donor lenticle into the eye during Descemet's stripping associated endothelial keratoplasty (DSAEK) or Descemet's membrane endothelial keratoplasty (DMEK) and penetrating keratoplasty (PK). The HPMC and/or CPMC component(s) will lubricate and add viscosity, protecting the cornea during storage, processing and subsequent transplant surgery. The liquid composition to be employed in the new invention is similar to that which was previously disclosed in U.S. Pat. No. 7,820,639 for several in vivo uses. It is novel and not obvious to use solutions of this type for in vitro corneal preservation of whole globes, excised corneas, sclera, conjunctiva, iris, the natural lens, retina, choroid and every other eye tissue and eye cells. However, the primary purpose within this embodiment is eye banking and corneal preservation, and in vitro use. The purpose of the glycerol component is to enhance tissue, endothelial and epithelial protection through enhanced lubrication, hydration control and osmoprotection. This should result in healthier cells to transplant, thinner donor corneas, and a healthier endothelium and epithelium. Any and all of these results will facilitate transplant success.

While the invention has been described in detail and with reference to specific embodiments thereof, it will be apparent to one skilled in the art that various changes and modifications can be made without departing from the spirit and scope of the invention.

Various modifications can be made to the present invention without departing from the apparent scope thereof.

It is claimed:

1. A method of preserving tissue, the method comprising the steps of:
   providing excised mammalian tissue to be preserved;
   providing a liquid composition including glycerol in a concentration of from 0.1% to 5.0%, dextran in a concentration of from 1.0% to 10.0%, chondroitin sulfate in a concentration of from 0.1% to 5.0%, and water; and
   placing the excised mammalian tissue to be preserved into the liquid composition under in vitro conditions.

2. The method of claim 1, wherein the excised mammalian tissue to be preserved is ophthalmic tissue.

3. The method of claim 2, wherein ophthalmic tissue to be preserved is corneal tissue.

4. The method of claim 3, wherein corneal tissue to be preserved is a cornea.

5. The method of claim 1, wherein the liquid composition and tissue to be preserved are stored at a temperature of about 0° C.-40° C.

6. The method of claim 1, further comprising the step of replenishing the liquid composition in which the tissue to be preserved is placed.

7. The method of claim 6, wherein the step of replenishing is a batch replenishment.

8. The method of claim 6, wherein the step of replenishing is a continuous replenishment.

9. The method of claim 4, wherein the cornea is placed in a volume of from about 50 ml to about 500 ml of the liquid composition.

10. The method of claim 1, further comprising the step of subsequently implanting the excised mammalian tissue preserved in the liquid composition.

11. The method of claim 10, wherein the tissue is a cornea.

12. The method of claim 1, wherein the liquid composition is an ophthalmic composition consisting essentially of glycerol in a concentration of from 0.1% to 5.0%, dextran in a concentration of from 1.0% to 10.0%, chondroitin sulfate in a concentration of from 0.1% to 5.0%, and water.

13. The method of claim 12, wherein the liquid composition is an ophthalmic composition and glycerol is present in a concentration of from 0.3% to 1.7%, dextran is present in a concentration of from 3.0% to 7.0%, and chondroitin sulfate is present in a concentration of from 0.5% to 4.5%.

14. The method of claim 12, wherein the liquid composition is an ophthalmic composition and glycerol is present in a concentration of from 0.6% to 1.4%, dextran is present in a concentration of from 4.0% to 6.0%, and chondroitin sulfate is present in a concentration of from 1.5% to 3.5%.

15. The method of claim 12, wherein the liquid composition is an ophthalmic composition and glycerol is present in a concentration of from 0.8% to 1.2%, dextran is present in a concentration of from 4.5% to 5.5%, and chondroitin sulfate is present in a concentration of from 2.0% to 3.0%.

16. The method of claim 15, wherein the liquid composition is an ophthalmic composition and chondroitin sulfate is present in a concentration of from 2.3% to 2.7%.

17. The method of claim 12, wherein the liquid composition is an ophthalmic composition and glycerol is present in a concentration of 1.0%, dextran is present in a concentration of 5.0%, and chondroitin sulfate is present in a concentration of 2.5%.

18. The method of claim 1, wherein the liquid composition is an ophthalmic composition consisting essentially of: glycerol in a concentration of from 0.1% to 5.0%, dextran in a concentration of from 1.0% to 10.0%, chondroitin sulfate in a concentration of from 0.1% to 5.0%, water, a buffer, and pH 6 to 8.

19. The method of claim 18, wherein the liquid composition is an ophthalmic composition and the pH of the composition is from 7.0 to 7.4.

20. The method of claim 18, wherein the liquid composition is an ophthalmic composition and glycerol is present in a concentration of from 0.3% to 1.7%, dextran is present in a concentration of from 3.0% to 7.0%, and chondroitin sulfate is present in a concentration of from 0.5% to 4.5%.

21. The method of claim 18, wherein the liquid composition is an ophthalmic composition and glycerol is present in a concentration of from 0.6% to 1:4%, dextran is present in a concentration of from 4.0% to 6.0%, and chondroitin sulfate is present in a concentration of from 1.5% to 3.5%.

22. The method of claim 18, wherein the liquid composition is an ophthalmic composition and glycerol is present in a concentration of from 0.8% to 1.2%, dextran is present in a concentration of from 4.5% to 5.5%, and chondroitin sulfate is present in a concentration of from 2.0% to 3.0%.

23. The method of claim 22, wherein the liquid composition is an ophthalmic composition and chondroitin sulfate is present in a concentration of from 2.3% to 2.7%.

24. The method of claim 18, wherein the liquid composition is an ophthalmic composition and glycerol is present in a concentration of 1.0%, dextran is present in a concentration of 5.0%, and chondroitin sulfate is present in a concentration of 2.5%.

25. The method of claim 18, wherein the liquid composition is an ophthalmic composition and the buffer is sodium borate and boric acid.

26. The method of claim 1, wherein the liquid composition is an ophthalmic composition consisting of glycerol in a concentration of from 0.1% to 5.0%, dextran in a concentration of from 1.0% to 10.0%, chondroitin sulfate in a concentration of from 0.1% to 5.0%, and water.

27. The method of claim 26, wherein the liquid composition is an ophthalmic composition and glycerol is present in a concentration of from 0.3% to 1.7%, dextran is present in a concentration of from 3.0% to 7.0%, and chondroitin sulfate is present in a concentration of from 0.5% to 4.5%.

28. The method of claim 26, wherein the liquid composition is an ophthalmic composition and glycerol is present in a concentration of from 0.6% to 1.4%, dextran is present in a concentration of from 4.0% to 6.0%, and chondroitin sulfate is present in a concentration of from 1.5% to 3.5%.

29. The method of claim 26, wherein the liquid composition is an ophthalmic composition and glycerol is present in a concentration of from 0.8% to 1.2%, dextran is present in a concentration of from 4.5% to 5.5%, and chondroitin sulfate is present in a concentration of from 2.0% to 3.0%.

30. The method of claim 26, wherein the liquid composition is an ophthalmic composition and chondroitin sulfate is present in a concentration of from 2.3% to 2.7%.

31. The method of claim 26, wherein the liquid composition is an ophthalmic composition and glycerol is present in a concentration of 1.0%, dextran is present in a concentration of 5.0%, and chondroitin sulfate is present in a concentration of 2.5%.

32. The method of claim 1, wherein the liquid composition further includes from about 0.01% to about 20% of mannitol.

33. The method of claim 1, wherein the liquid composition further includes about 0.5% of mannitol.

34. The method of claim 1, wherein the excised mammalian tissue is ophthalmic tissue which is excised from a mammalian donor, preserved in vitro, and subsequently implanted into a recipient.

* * * * *